United States Patent
Berg et al.

(10) Patent No.: US 6,235,054 B1
(45) Date of Patent: May 22, 2001

(54) GRAFTS WITH SUTURE CONNECTORS

(75) Inventors: Todd Allen Berg, Lino Lakes; Jon Patrick St. Germain, Elk River, both of MN (US)

(73) Assignee: St. Jude Medical Cardiovascular Group, Inc., Minneapolis, MN (US)

(*) Notice: Subject to any disclaimer, the term of this patent is extended or adjusted under 35 U.S.C. 154(b) by 0 days.

(21) Appl. No.: 09/032,270

(22) Filed: Feb. 27, 1998

(51) Int. Cl.$^7$ .................................................. A61F 2/00
(52) U.S. Cl. ........................................... 623/1.36; 606/153
(58) Field of Search .......................... 623/1, 12, 1.36; 606/153, 213, 214, 215

(56) References Cited

U.S. PATENT DOCUMENTS

| | | | |
|---|---|---|---|
| 4,214,587 | 7/1980 | Sakura | 128/334 R |
| 4,459,252 | 7/1984 | MacGregor | 264/46.9 |
| 4,487,567 | 12/1984 | Possis et al. | 425/403 |
| 4,503,569 | 3/1985 | Dotter | 3/1.4 |
| 4,546,499 | 10/1985 | Possis et al. | 623/1 |
| 4,562,597 | 1/1986 | Possis et al. | 623/1 |
| 4,592,754 | 6/1986 | Gupte et al. | 623/1 |
| 4,601,718 | 7/1986 | Possis et al. | 623/1 |
| 4,605,406 | 8/1986 | Cahalan et al. | 623/1 |
| 4,617,932 | 10/1986 | Kornberg | 128/334 R |
| 4,629,458 | 12/1986 | Pinchuk | 623/1 |
| 4,632,842 | 12/1986 | Karwoski et al. | 427/2 |
| 4,657,544 | 4/1987 | Pinchuk | 623/1 |
| 4,665,906 | 5/1987 | Jervis | 128/92 YN |
| 4,718,907 | 1/1988 | Karwoski et al. | 623/12 |
| 4,733,665 | 3/1988 | Palmaz | 128/343 |
| 4,738,740 | 4/1988 | Pinchuk et al. | 156/167 |
| 4,743,252 | 5/1988 | Martin, Jr. et al. | 623/1 |
| 4,759,757 | 7/1988 | Pinchuk | 623/1 |
| 4,787,899 | 11/1988 | Lazarus | 623/1 |
| 4,798,606 | 1/1989 | Pinchuk | 623/1 |
| 4,892,539 | 1/1990 | Koch | 623/1 |
| 4,909,979 | 3/1990 | Possis et al. | 264/571 |
| 4,955,899 | 9/1990 | Della Corna et al. | 623/1 |
| 5,037,377 | 8/1991 | Alonso | 600/36 |
| 5,061,275 | 10/1991 | Wallsten et al. | 623/1 |
| 5,084,065 | 1/1992 | Weldon et al. | 623/1 |
| 5,100,422 | 3/1992 | Berguer et al. | 606/151 |
| 5,104,399 | 4/1992 | Lazarus | 623/1 |
| 5,104,400 | 4/1992 | Berguer et al. | 264/132 |
| 5,116,360 | 5/1992 | Pinchuk et al. | 623/1 |
| 5,122,154 | 6/1992 | Rhodes | 606/198 |
| 5,135,467 | 8/1992 | Citron | 600/16 |
| 5,152,782 | 10/1992 | Kowligi et al. | 623/1 |
| 5,163,951 | 11/1992 | Pinchuk et al. | 623/1 |
| 5,211,658 | 5/1993 | Clouse | 623/1 |
| 5,211,683 | 5/1993 | Maginot | 128/898 |
| 5,246,451 | 9/1993 | Trescony et al. | 623/1 |
| 5,246,452 | 9/1993 | Sinnott | 623/1 |
| 5,275,622 | 1/1994 | Lazarus et al. | 623/1 |
| 5,282,847 | 2/1994 | Trescony et al. | 623/1 |

(List continued on next page.)

FOREIGN PATENT DOCUMENTS

| | | | |
|---|---|---|---|
| 670239 | 1/1994 | (AU) | A61F/2/06 |
| 539237 | 4/1993 | (EP) | A61F/2/06 |
| 637454 | 2/1995 | (EP) | A61M/25/10 |
| 680734 | 11/1995 | (EP) | A61F/2/06 |
| 684022 | 11/1995 | (EP) | A61F/2/06 |
| WO 94/06372 | 3/1994 | (WO) | A61F/2/04 |
| WO 96/01591 | 1/1996 | (WO) | A61B/17/22 |
| WO 96/01599 | 1/1996 | (WO) | A61F/2/06 |
| WO 96/18361 | 6/1996 | (WO) | A61F/2/06 |
| WO 97/13463 | 4/1997 | (WO) | A61B/17/00 |
| WO 97/13471 | 4/1997 | (WO) | A61B/19/00 |

*Primary Examiner*—Michael J. Milano
(74) *Attorney, Agent, or Firm*—Fish & Neave; Robert R. Jackson

(57) ABSTRACT

A graft for use in vascular anastomosis is provided. The graft includes a cylindrical metal braided frame and suture retention structures at the ends of the braided frame which provide suture sites for anastomosis.

12 Claims, 3 Drawing Sheets

U.S. PATENT DOCUMENTS

| | | | |
|---|---|---|---|
| 5,304,220 | 4/1994 | Maginot | 623/1 |
| 5,306,240 | 4/1994 | Berry | 604/51 |
| 5,316,023 | 5/1994 | Palmaz et al. | 128/898 |
| 5,354,336 | 10/1994 | Kelman et al. | 623/6 |
| 5,360,443 | 11/1994 | Barone et al. | 623/1 |
| 5,366,504 | 11/1994 | Andersen et al. | 623/11 |
| 5,387,235 | 2/1995 | Chuter | 623/1 |
| 5,397,345 | 3/1995 | Lazarus | 623/1 |
| 5,413,598 | 5/1995 | Moreland | 623/1 |
| 5,425,765 | 6/1995 | Tiefenbrun | 623/12 |
| 5,429,144 | 7/1995 | Wilk | 128/898 |
| 5,443,497 | 8/1995 | Venbrux | 623/1 |
| 5,443,499 | 8/1995 | Schmitt | 623/1 |
| 5,456,712 | 10/1995 | Maginot | 623/1 |
| 5,480,423 | 1/1996 | Ravenscroft et al. | 623/1 |
| 5,489,295 | 2/1996 | Piplani et al. | 623/1 |
| 5,496,364 | 3/1996 | Schmitt | 623/1 |
| 5,496,365 | 3/1996 | Sgro | 623/1 |
| 5,507,769 | 4/1996 | Marin et al. | 606/198 |
| 5,509,931 | 4/1996 | Schmitt | 623/1 |
| 5,522,880 | 6/1996 | Barone et al. | 623/1 |
| 5,545,214 | 8/1996 | Stevens | 623/2 |
| 5,562,725 | 10/1996 | Schmitt et al. | 623/1 |
| 5,584,875 | 12/1996 | Duhamel et al. | 623/1 |
| 5,584,876 | 12/1996 | Bruchman et al. | 623/1 |
| 5,607,463 | 3/1997 | Schwartz et al. | 623/1 |
| 5,607,464 | 3/1997 | Trescony et al. | 623/1 |
| 5,609,624 | 3/1997 | Kalis | 623/1 |
| 5,628,782 | 5/1997 | Myers et al. | 623/1 |
| 5,628,786 | 5/1997 | Banas et al. | 623/1 |
| 5,628,788 | 5/1997 | Pinchuk | 623/1 |
| 5,632,772 | 5/1997 | Alcime et al. | 623/1 |
| 5,653,747 | 8/1997 | Dereume | 623/1 |
| 5,667,523 * | 9/1997 | Bynon | 623/12 |
| 5,683,453 * | 11/1997 | Palmaz | 606/153 |
| 5,693,089 * | 12/1997 | Inoue | 623/12 |
| 5,695,504 | 12/1997 | Gifford, III et al. | 606/153 |
| 5,733,327 * | 3/1998 | Igaki | 623/1 |
| 5,824,066 * | 10/1998 | Gross | 623/2 |
| 5,972,017 | 10/1999 | Berg et al. | 606/198 |
| 5,976,178 | 11/1999 | Goldsteen et al. | 623/1 |
| 6,001,124 | 12/1999 | Bachinski | 623/1 |

\* cited by examiner

GRAFTS WITH SUTURE CONNECTORS

BACKGROUND OF THE INVENTION

This invention relates to grafts for use in the repair, replacement or supplement of a medical patient's natural body organ structures or tissues. More particularly, this invention relates to a graft with a suture connector for use in vascular anastomosis (the surgical connection of vessels).

An example of the possible uses of the invention is a minimally invasive cardiac bypass procedure. This and other examples are considered in detail in David S. Goldsteen et al., U.S. patent application Ser. No. 08/745,618, filed Nov. 7, 1996, which is incorporated herein by reference.

Vascular anastomosis is a delicate and time-consuming procedure. Conventional anastomosis using a graft requires placement of fine sutures circumferentially around the vessel at the anastomosis (vessel attachment) site.

Conventional anastomosis using graft suturing, as shown in FIG. 1a, may have certain limitations. First, the anastomosis created may be non-compliant (i.e., the graft may not readily expand or contract radially). This may produce a compliance mis-match between the graft and the native vessel. As the native vessel expands or contracts under hemodynamic pressure, the suture site tends to remain more nearly rigid, producing high stress which may eventually result in tissue and/or graft deterioration, as shown for the graft in FIG. 1b. Second, the selection of materials for grafts is necessarily limited to those materials of sufficient tensile strength in order to withstand suturing. For example, a well-known bio-compatible and bio-stable material such as silicone has not been used to its full potential in grafts because of its limited mechanical ability to retain sutures.

In view of the foregoing, it is an object of the present invention to provide a graft which is compliant at the anastomosis site.

It is also an object of the present invention to provide a graft which is formed from a material which is bio-compatible and bio-stable.

SUMMARY OF THE INVENTION

These and other objects are accomplished by providing a graft for use in vascular anastomosis comprising a generally cylindrical metal braided frame and suture retention structures at distal ends of the braided frame which provide suture sites for anastomosis.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout and in which.

DETAILED DESCRIPTION OF THE INVENTION

Figure 1A:
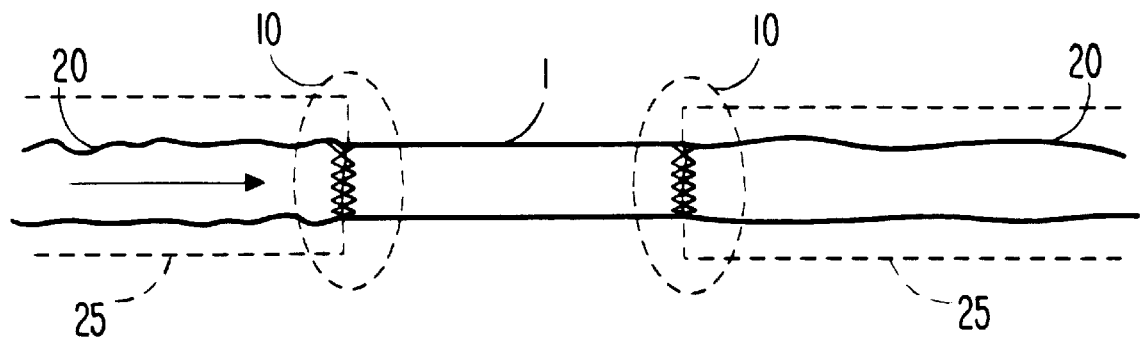
FIG. 1a is a simplified elevational view showing conventional anastomosis using graft suturing.
Figure 1B:
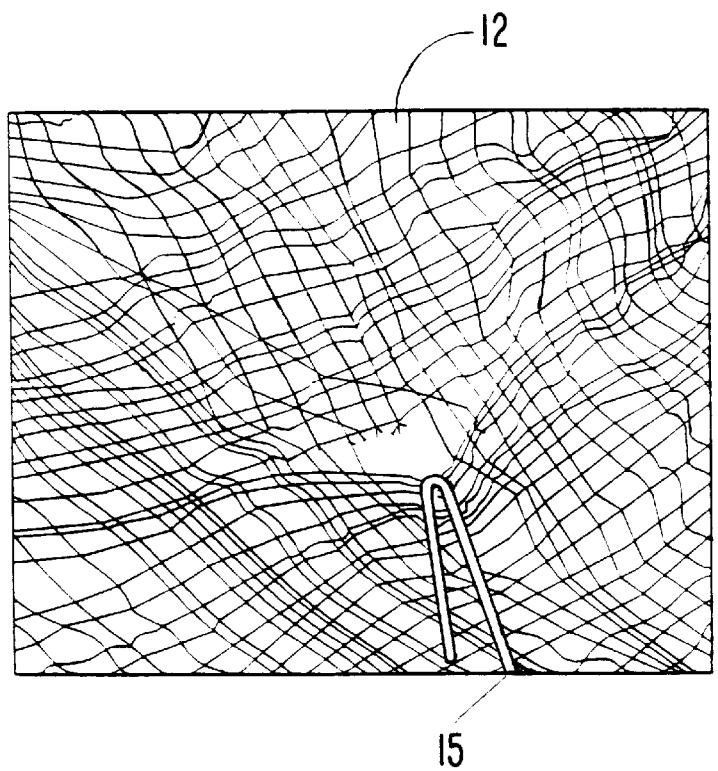
FIG. 1b is a simplified elevational view showing tissue and graft damage that results with a conventional graft when the adjacent native vessel expands or contracts under hemodynamic pressure.

As has been mentioned, conventional anastomosis using graft suturing, as shown in FIG. 1a, may have the disadvantage that the anastomosis created may be relatively non-compliant (i.e., graft 1 can not expand or contract radially). Native vessel 20 is shown in its "rest" state as indicated by reference numeral 20 and in its "expanded" state as indicated by reference numeral 25. (Of course, native vessel 20 can also contract but this "contracted" state is not shown in FIG. 1a, for clarity.) This expansion and contraction may produce a compliance mis-match between graft 1 and the native vessel 20. As native vessel 20 expands or contracts under hemodynamic pressure, suture site 10 remains rigid, producing high stress and, eventually, tissue and graft damage as suture thread 15 pulls through material 12 (e.g., woven polyester or non-woven PTFE (Teflon)) of graft 1, as shown in FIG. 1b. Second, the material selected for graft 1 is necessarily limited to those materials of tensile strength sufficient to withstand suturing. For example, a well-known bio-compatible and bio-stable material such as silicone has not been used in grafts because of its limited mechanical ability to retain sutures.

Figure 2A:
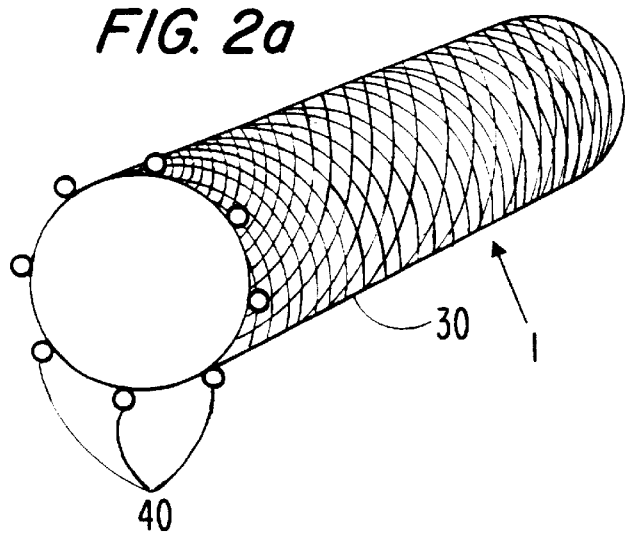
FIG. 2a is a simplified perspective view showing a graft for use in vascular anastomosis according to the present invention.

FIG. 2a shows graft 1 for use in vascular anastomosis according to the present invention. Graft 1 includes cylindrical metal braided frame 30 (preferably formed from a compliant material such as a nickel titanium alloy), and suture retention structures at distal ends of the frame which provide suture sites 10 for anastomosis. The suture retention structures are preferably metal loops 40 coupled to distal ends of braided frame 30.

Figure 2B:
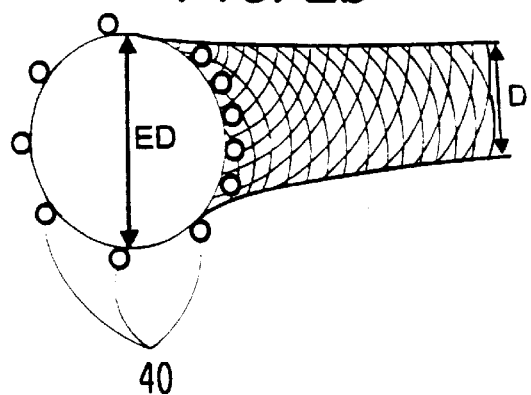
FIG. 2b is another view similar to FIG. 2a showing a graft for use in vascular anastomosis according to the present invention.

Metal loops 40 of the suture retention structures can be coupled to distal ends of braided frame 30 such that the openings of metal loops 40 are at any angle to the central axis of the frame. For example, metal loops 40 of the suture retention structures can be coupled to distal ends of braided frame 30 such that the openings of metal loops 40 are substantially perpendicular to the central axis of the frame. As shown in FIG. 2b, such an arrangement facilitates expanding the diameter ED the mouth of graft 1 (e.g., from an un-expanded diameter D of 4 mm to an expanded diameter ED of 5 mm) to provide optimal anastomosis. Alternatively, metal loops 40 of the suture retention structures can be coupled to distal ends of braided frame 30 such that the openings of metal loops 40 are substantially parallel to the central axis of the frame.

Figure 3A:
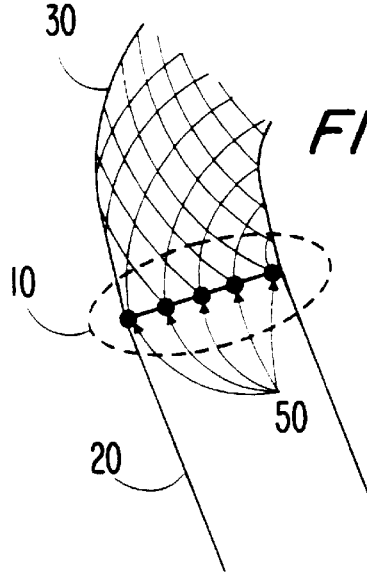
FIGS. 3a and 3b are simplified elevational views showing a graft for use in vascular anastomosis according to the present invention and an expanded view of a single loop on such a graft, respectively.
Figure 3B:
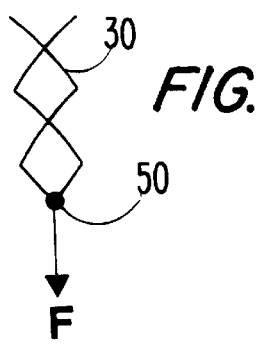

Metal braided frame 30 preferably includes welds 50 at distal ends to prevent unraveling. As shown in FIG. 3a, welded ends 50 of frame 30 can serve as suture retention structures for coupling to native vessel 20. For example, given a 36 strand, 4 mm graft, suture spacing would be 0.028 inches (18 sutures). Other possible strand sizes include 8, 16, 32, 64 and 72, each with corresponding graft sizes and suture spacing. FIG. 3b shows an expanded view of a single braid loop with welded end 50 and the direction of the principal force acting on that welded end.

Figure 4:
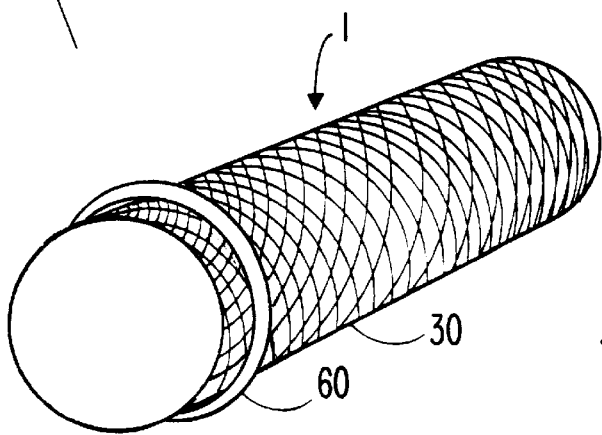
FIG. 4 is another view similar to FIG. 2a showing another illustrative graft for use in vascular anastomosis according to the present invention and including a suture retention ring.

The suture retention structures can also include suture rings 60, as shown in FIG. 4, which are radially offset from frame 30. Suture rings 60 can be made of metal, polyester or resilient polymer, for example, and are coupled to distal ends of frame 30. Suture rings 60 are preferably constructed as disclosed in commonly assigned Berg et al. U.S. patent application Ser. No. 09/016,721, filed Jan. 30, 1998, incorporated herein by reference. The advantage of using suture rings 60 is that they help to absorb the stress of the forces acting on anastomosis site 10, allowing any covering (for example, polymer) to be essentially stress free. Thus the covering is no longer limited by mechanical suture strength.

Figure 5A:
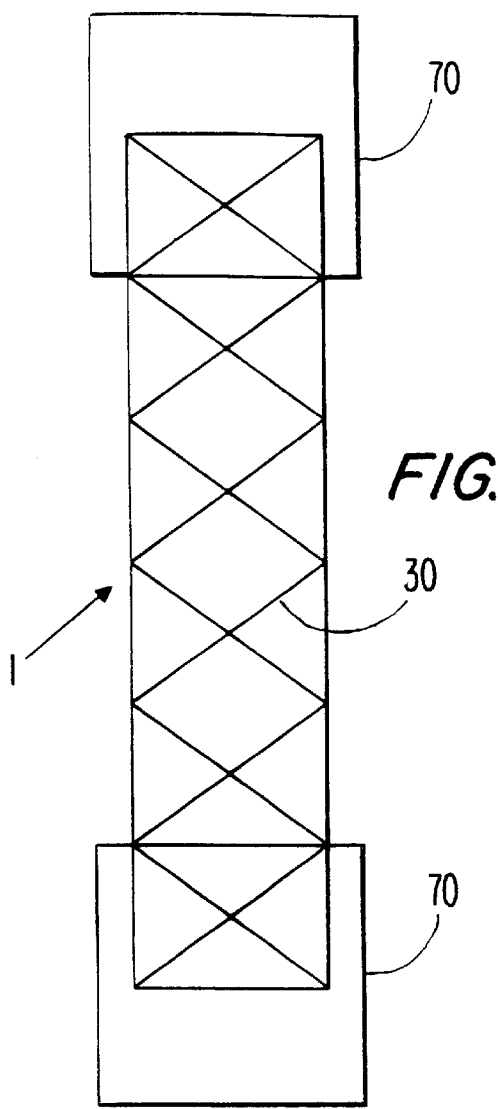
FIGS. 5a and 5b are simplified elevational views showing still another illustrative graft for use in vascular anastomosis according to the present invention and including a polymer cap, before and after fusing of the polymer cap, respectively.
Figure 5B:
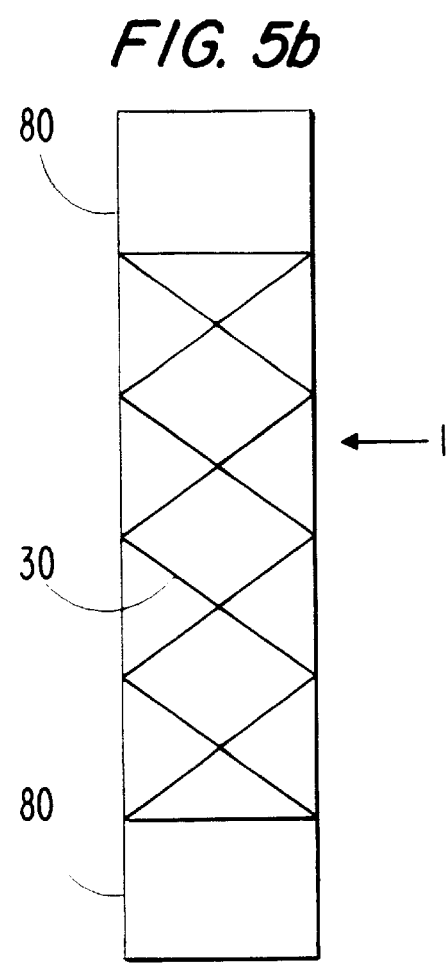

Suture retention structures can also include polymer caps 80 fused to distal ends of frame 30. FIGS. 5a and 5b show graft 1 for use in vascular anastomosis according to the present invention including a polymer cap, before (reference numeral 70) and after (reference numeral 80) fusing, respectively. To minimize added rigidity, polymer caps 80 are kept relatively short.

In order to provide radiopacity to anastomosis site 10, the suture retention structures can be plated. Plating provides a visual marker if future access to the site is needed.

The graft 1, including the suture retention structures, can also be coated with a bio-compatible and bio-stable material such as silicone.

Thus, it is seen that a graft is provided in which is compliant at the anastomosis site. In addition, the graft can be formed from a material which is bio-compatible and bio-stable. One skilled in the art will appreciate that the present invention can be practiced by other than the described embodiments, which are presented for purposes of illustration and not of limitation, and the present invention is limited only by the claims which follow.

What is claimed is:

1. A graft for use in vascular anastomosis comprising:
   a cylindrical metal braided frame; and
   suture retention structures at distal ends of said braided frame which provide suture sites for anastomosis wherein
   said suture retention structures include suture rings; and
   said suture rings are metal and are welded to distal ends of said frame.

2. A graft for use in vascular anastomosis comprising:
   a cylindrical metal braided frame; and
   suture retention structures at distal ends of said braided frame which provide suture sites for anastomosis wherein
   said cylindrical metal braided frame includes welds at distal ends to prevent frame unraveling;
   said graft is coated with a bio-compatible and bio-stable material; and
   said braided frame is formed from a compliant material.

3. The graft of claim 2 wherein said suture retention structures include metal loops coupled to distal ends of said braided frame.

4. The graft of claim 2 wherein said suture retention structures include suture rings.

5. The graft of claim 3 wherein said suture rings are metal and are welded to distal ends of said frame.

6. The graft of claim 3 wherein said suture rings are polyester and are coupled to distal ends of said frame.

7. The graft of claim 3 wherein said suture rings are resilient polymer and are coupled to distal ends of said frame.

8. The graft of claim 2 wherein said suture retention structures include polymer caps fused to distal ends of said frame.

9. The graft of any one of claims 1 and 2 through 8 wherein said graft is coated with a bio-compatible and bio-stable material.

10. The graft of any one of claims 1 and 2 through 8 wherein said graft is coated with silicone.

11. The graft of any one of claims 1 and 2 through 8 wherein said braided frame is formed from a compliant material.

12. The graft of any one of claims 1 and 2 through 8 wherein said suture retention structures are plated to provide radiopacity to the anastomosis site.

* * * * *